United States Patent [19]
Bartek et al.

[11] 4,094,922
[45] June 13, 1978

[54] ALKYLATION OF AROMATICS USING AMPHORA SHAPED CATALYSTS

[75] Inventors: Joseph P. Bartek, University Heights; Robert K. Grasselli, Chagrin Falls, both of Ohio

[73] Assignee: Standard Oil Company, Cleveland, Ohio

[21] Appl. No.: 771,482

[22] Filed: Feb. 24, 1977

Related U.S. Application Data

[63] Continuation of Ser. No. 550,892, Feb. 18, 1975, abandoned.

[51] Int. Cl.² .............................................. C07C 3/52
[52] U.S. Cl. .......................... 260/671 C; 252/477 R; 260/671 R

[58] Field of Search ................. 260/671 R, 671 C; 252/477 R

[56] References Cited

U.S. PATENT DOCUMENTS

| | | | |
|---|---|---|---|
| 3,347,798 | 10/1967 | Baer et al. | 252/477 |
| 3,798,176 | 3/1974 | Ao | 252/477 |

*Primary Examiner*—Delbert E. Gantz
*Assistant Examiner*—C. E. Spresser
*Attorney, Agent, or Firm*—Herbert D. Knudsen; William D. Mooney

[57] ABSTRACT

Catalysts having a substantially spherical shape, a void center and a hole in the external surface communicating to the void center have been found to be especially effective in the alkylation of aromatic hydrocarbons.

11 Claims, 1 Drawing Figure

U.S. Patent June 13, 1978 4,094,922
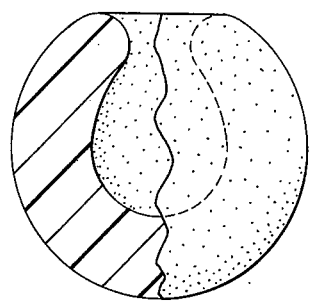

ALKYLATION OF AROMATICS USING AMPHORA SHAPED CATALYSTS

This is a continuation, of application Ser. No. 550,892 filed Feb. 18, 1975 now abandoned.

BACKGROUND OF THE INVENTION

The alkylation of aromatic hydrocarbons is well known in the art. See for example, U.S. Pat. No. 3,751,506 that shows a vapor phase alkylation in the presence of aluminosilicate catalysts in the extrudate form. The present invention can use the same alkylation reaction conditions and catalyst compositions as are shown in the art.

The amphora form of an aggregate is shown by Callahan, Miller and Shaw in U.S. Pat. No. 3,848,033. The techniques employed in this patent are directly applicable to the production of amphora shaped alkylation catalysts and supports.

SUMMARY OF THE INVENTION

The invention is in the process for the alkylation of aromatic hydrocarbons wherein the aromatic hydrocarbon is contacted with an alkylating agent in the presence of an acid catalyst at an elevated temperature, the improvement comprising
    using as at least part of the catalyst an amphora catalyst having a substantially spherical shape, a void center and a hole in the external surface of the catalyst communicating to the void center.

Use of amphora shaped catalysts gives significant advantages in the areas of catalyst life, yields of products and increased efficiency.

DESCRIPTION OF THE DRAWING

The amphora form of the catalyst is shown in the FIGURE. It is seen that the catalyst from the outside looks like a sphere with a hole in it. From the cut-away section, it is seen that the interior of the sphere is void and that the hole in the external surface of the sphere communicates to this void center.

DETAILED DESCRIPTION OF THE INVENTION

The central feature of the invention is the catalyst form. This amphora catalyst form can be made from any catalyst used in alkylation reactions by applying the techniques disclosed in U.S. Pat. No. 3,848,033. Broadly, these preparations involve dropping droplets of a slurry onto a particle bed to form the amphora.

When the droplet contacts the particle bed, it is, of course, spherical. Broadly, the nature of the particle bed or the conditions of the particle bed, including heat or other source of drying, are adjusted so that most, but not all, of the external surface becomes set, i.e. the suspending liquid of the slurry is removed. The suspended particles in the slurry then migrate to this set outer surface, and a void center is formed. In a similar manner, the portion of the external surface of the spherical droplet that was not originally dried migrates to the interior of the droplet. This migration "pulls" a hole from the external surface of the droplet to the void center.

The amphora shape can be obtained using a wide range of slurries and particle beds. A hydrophobic or hydrophilic particle bed can be employed to prepare the amphora. The specific techniques may vary to some extent as different slurries and particle beds are employed, but the amphora is believed to be made in each case as described above. The amphora made by this process may have any size, but amphora having a diameter of 1 to about 10 mm. are normally used.

The alkylation of aromatics process in which the amphora are used is substantially the same using the amphora shaped catalyst even though improved results are obtained by the use of the amphora. The catalyst may be any of the catalysts employed in the art. These are normally acid catalysts such as zeolite catalysts, and other solid or liquid acids such as phosphoric acid, amorphous silicaalumina, heteropolyacids, isopolyacids, other acid salts and Lewis acids such as aluminum chloride. These acids are normally supported on carriers such as $SiO_2$, $Al_2O_3$, $SiO_2$-$Al_2O_3$, $TiO_2$, $ZrO_2$, kieselguhr, montmorillonite, $AlPO_4$, $CaAl_2O_4$, $BPO_4$ and the like. As alkylating agents, olefins, alcohols, aldehydes and the like can be used. The reaction may be conducted at temperatures of 50° to 600° C. at atmospheric, superatmospheric or subatmospheric pressure. The alkylation of benzene with olefins, especially with ethylene, is preferred.

Using the amphora, however, very desirable results from the process are obtained. The amount of amphora shaped catalyst that can be employed may vary widely. The alkylation catalyst can be essentially all amphora, but normally more than 25% by volume of the catalyst is the amphora shape.

SPECIFIC EMBODIMENTS

Comparative EXAMPLE A and EXAMPLE 1 - Catalyst preparations

Amphora Preparation

A mordenite-alumina amphora alkylation catalyst in the amphora form was prepared by making a slurry containing 15 g. of mordenite alumino-silicate, that had been washed with 150 cc. of 6 normal hydrochloric acid, and 15 g. Dispal alumina hydrate in 17.5 cc. of distilled water. Concentrated nitric acid (0.3 cc.) was added to disperse the alumina hydrate. The slurry was stirred vigorously. An additional 21 cc. of water was added to bring the consistency of the slurry to the desired level after vigorous stirring. The slurry was allowed to age for four days and 10 cc. of water was added to bring the slurry to the desired consistency. The slurry was then dropped onto a fluorinated graphite powder particle bed supported on a velvet cloth. Heat was applied to the particle bed. The amphora had a diameter of 3 mm. and a wall thickness of 0.7 mm. The amphora were dried at 100° C. overnight and calcined at 425° C. for three hours. After the heat treatment, the amphora were washed with large amounts of water, dried at 100° C. and again calcined at 425° C. for 3½ hours.

Extrudate Preparation

In the same manner as described above, a slurry was made containing identical quantities of acid-washed mordenite, Dispal and nitric acid in 31 cc. of water, and a paste was made of the slurry by drying the slurry. The paste was extruded from a plastic syringe and dried to form 1.5 mm. diameter pellets 3–6 mm. long. The other properties of the catalysts are shown in Table 1 below.

Table 1

| Property | Catalyst Properties | |
|---|---|---|
| | Amphora | Extrudate |
| Na, wt. % | <0.003 | <0.003 |
| Surface Area, m.²/g. | 363 | 363 |

It is believed that these two catalysts would provide a suitable comparison of the amphora over the extrudate because they have identical compositions and surface areas, and differ in size and shape.

Comparative EXAMPLE B and EXAMPLE 2 - Comparison of catalysts in alkylation of benzene The catalysts prepared above were compared in the alkylation of benzene with ethylene to obtain ethylbenzene. A fixed-bed reactor was constructed of a 1.9 cm. inside diameter stainless steel tube having a reaction zone of 30 cc. and separate inlets for benzene and ethylene. The reaction was conducted using a benzene/ethylene molar ratio of 5 and a dilution with nitrogen to bring the contact time to one second. The reaction was conducted under a pressure of 75 p.s.i.g. using a benzene liquid space velocity of 20. The reactor was charged with 12.1 g. of the amphora shaped catalyst for the example of the invention, and 13.3 g. of the extrudate catalyst for the comparative example. At a temperature of 315° C., the reaction was run for 10 minutes, and then the liquid product was collected for 25 minutes. Under these conditions, the results obtained with the amphora and extrudate had substantially the same performance giving a liquid product containing 18.6% ethylbenzene and a conversion of ethylene to ethylbenzene of 73%.

Using the same catalysts without regeneration, the temperature was increased to 400° C. After a 10-minute prerun at this temperature, a 25-minute recovery run was made. The amphora for the example of the invention at the higher temperature showed a clear superiority giving 16% ethylbenzene in the liquid product as compared to only 7.2% ethylbenzene with the extrudate which represents Comparative Example B.

Comparative EXAMPLES C-E and EXAMPLES 3-6 - Comparative activity of amphora catalysts with time The catalysts prepared above were diluted with Alundum so that 7.3 g. of each catalyst was present in the 30 cc. reaction zone of the reactor. Before reaction, they were both regenerated in air at 480° C. for two hours. The conditions of the reaction were identical to the example above using an inlet temperature of 315° C. except that the weight of benzene per weight of active catalyst per hour was 71. The total reaction time was about two hours and three samples of the product were collected by recovering all of the product during three 25-minute periods at equal time intervals. Table 2 shows the results of these experiments with the time of the sample midpoint and in terms of the percent of the ethylene converted to ethylbenzene. Since the weight hourly space velocity is increased by about two, the initial results in these experiments are lower than the results reported above.

Table 2
Comparison of Life of Amphora v. Extrudate in Alkylation of Benzene

| Comparison | Sample Time, Min. | Conversion, % | |
|---|---|---|---|
| | | Amphora | Extrudate |
| 3 | 22.5 | 43 | 42 |
| 4 | 57.5 | 35 | 24 |
| 5 | 96.5 | 27 | 13 |

Table 2 shows that the life of the extrudate is significantly shorter than that of the amphora. A calculation from these tests has been conducted to determine the half life of the catalysts, i.e. the time at which the catalyst loses half of its activity. For the amphora, the half life is 116 minutes, whereas the extrudate has a half life of 42 minutes.

In the same manner as shown above, other acid catalysts can be made in the amphora form and used in alkylation reactions. Also, other alkylation reactions, such as the alkylation of naphthalene with ethyl alcohol and the alkylation of benzene with propylene, can be conducted using the amphora catalysts.

We claim:

1. In a process for the alkylation of an aromatic hydrocarbon wherein the aromatic hydrocarbon is contacted with an alkylating agent in the presence of a fixed-bed acid catalyst at an elevated temperature, the improvement
wherein at least a part of said catalyst has the amphora shape and a diameter of 1–10 mm.

2. The process of claim 1 wherein the amphora catalyst is a zeolite catalyst.

3. A process of claim 1 wherein the amphora catalyst is an amorphous silica-alumina.

4. The process in claim 1 wherein the amphora catalyst is phosphoric acid, a heteropolyacid, an isopolyacid or an acidic salt supported on $SiO_2$, $SiO_2$—$Al_2O_3$, $Al_2O_3$, $AlPO_4$, $BPO_4$, $CaAl_2O_4$, $TiO_2$, $ZrO_2$, montmorillonite, kieselguhr or other suitable carrier.

5. A process in claim 1 wherein the amphora catalyst is a Lewis acid such as aluminum chloride supported on a suitable carrier.

6. The process of claim 1 wherein the aromatic hydrocarbon is benzene.

7. The process of claim 1 wherein the alkylating agent is an olefin.

8. The process of claim 1 wherein benzene is alkylated with ethylene.

9. The process in claim 1 wherein benzene is alkylated with propylene.

10. The process of claim 1 wherein more than 25% of the catalyst is the amphora catalyst.

11. The process of claim 1 wherein essentially all of the catalyst is the amphora catalyst.

* * * * *